United States Patent [19]

Funken et al.

[11] Patent Number: 6,107,480
[45] Date of Patent: Aug. 22, 2000

[54] METALLATED OR UNMETALLATED PORPHYRIN DERIVATIVES HAVING AMPHIPHILIC PROPERTIES

[75] Inventors: Karl-Heinz Funken, Bonn; Gerda Horneck, Bendorf; Barbara Milow, Köln; Manfred Schäfer, Wächtersbach; Claudia Schmitz, Frechen; Delia Faust, Eitorf; Jürgen Ortner, Köln; Michael Sattlegger, Bonn, all of Germany

[73] Assignee: DLR, Deutsche Zentrum fur Luft und Raumfahrt E.V., Germany

[21] Appl. No.: 09/115,678

[22] Filed: Jul. 15, 1998

[30] Foreign Application Priority Data

Jul. 16, 1997 [DE] Germany .......................... 197 30 469
Oct. 4, 1997 [DE] Germany .......................... 197 43 903

[51] Int. Cl.$^7$ .................................................. C07B 47/00
[52] U.S. Cl. .......................... 540/145; 514/183; 514/184; 514/185; 525/417; 204/157.5
[58] Field of Search ........................... 525/417; 540/145; 514/183, 184, 185; 204/157.5

[56] References Cited

U.S. PATENT DOCUMENTS

| 4,614,723 | 9/1986 | Schmidt et al. ........................ 436/536 |
| 5,236,914 | 8/1993 | Meunier et al. ........................ 514/185 |

FOREIGN PATENT DOCUMENTS

| 127797 | 5/1984 | European Pat. Off. . |
| 345171 | 12/1989 | European Pat. Off. . |
| 3836759 | 5/1990 | Germany . |
| 3924815 | 1/1991 | Germany . |
| 9300815 | 1/1993 | WIPO . |

OTHER PUBLICATIONS

Borisov, A.V. et al., "Photostimulated Emission of Singlet Oxygen Molecules into the Gas Phase from Tetra(m–butoxyphenyl)porphin Adsorbed on SiO$_2$" *Russian Journal of Physical Chemistry* 66 (2) 1992, pp. 307–308.

Eisenberg, Walter C. et al., "Atmoshpheric Gas Phase Generation of SInglet Oxygen by Homogeneous Photosynsitization" *Tetrahedron Letters*, vol. 31, No. 41 (1990) pp. 5857–5859.

Dahl, Thomas A. et al., "Pure Singlet Oxygen Cytotoxicity for Bacteria" *Photochemistry and Photogiology*, vol. 46 No. 3 (1987) pp. 345–352, 1987).

Banks, J.G. et al., "The Cytotoxic and Photodynamic Inactivation of Micro–Organisms by Rose Bengal", *Journal of Applied Bacteriology* vol. 58 (1985) pp. 391–400.

Kolega, M. et al., "Disinfection and Clarification of Treated Sewage by Advanced Microfiltration" *Wat. Sci. Tech.*, vol. 23 Kyoto (1991) pp. 1609–1618.

Dorau Wolfgang (1996) Mikrofiltration als Schlussreinigungbeider Abwasserreinigung, Notwendigkeit, Verfahrenstechnische Einbindung, Kosten, Gewässerscjitz-Awasser–Abwasser 152:51/1–28.

Acher, J.A. et al., "Destruction of Coliforms in Water an Sewage Water by Dye–Sensitized Photooxidation" *Applied and Envirnmental Microbiology*, vol. 33, No. 5 (May 1977) pp. 1019–1022.

Dahl, Thomas A. et al., "Comparison of Photodynamic Action By Rose Bengal in Gram–Positive Bacteria", *Photochemistry and Photobiology*, vol. 48, No. 5 (1988) pp. 607–612.

Acher, A. et al., "Photochemical Disinfection of Effluents–Pilot Plant Studies", *Wat Res.* vol. 24, No. 7 (1990) pp. 837–843.

Conn, Howard MD et al., "Iodine Disinfection of Hydrophilic Contact Lenses" *Annals of Ophthalmology* (Mar. 1981) pp. 361–364.

LeChevallier, Mark W. et al., "Enumerating Injured Coliforms in Drinking Water" *Journ. AWWA*, Jun. 1985, pp. 81–87.

Hegna, I.K. et al., "An Investigation of the Bactericidal and Fungicidal Effects of Certain Disinfectans by Use of a Capacity Test" *Ann. Inst. Pasteur/Microbiol.*, vol. 139 (1988) pp. 473–483.

Fuhrmann, Herbert et al., "Investigations on the Problem of Heat Activation of Bacterial Spores After Disinfection with Regard to a Decontamination Method of Equipment and Rooms by Aerosol" *ZBL Bakt. Hyg. B.* vol. 182, (1986) pp. 515–524.

Joyce, T.M. et al., "Inactivation of Fecal Bacteria in Drinking Water by Solar Heating", *Applied & Environmental Microbiology*, vol. 62, No. 2 (Feb. 1996) pp. 399–402.

Niederwohrmeier, B. et al., "Microwave Treatment as an Alternative Pasteurisation Process for the Disinfection of Sewage Sludge—Experiences with the Treatment of Liquid Manure", in *Inactivation of Microorganisms in Sewage Sludge by Stabilization Processes*, D Strauch, et al., eds., Elsevier Applied Science, London, pp. 135–147 (1935).

Polyzois, Gregory L. et al., "The Effect of Glutaraldehyde and Microwave Disinfection on Some Properties of Acrylic Denture Resin" *The International Journal of Prosthodontics*, vol. 8, No. 2 (1995) pp. 150–154.

Ahlstrom, Scott B. "Irradiation of Municipal Sludge for Pathogen Control: Why or Why Not?" *Radiat. Phys. Chem.*, vol. 31, No. 1–3, (1988) pp. 131–138.

Myhrstad, Jan Aug "Disinfection of Sewage by Ultraviolet Irradiation" *NIPH Annals*, vol. 2, No. 2 (Dec. 1979) pp. 11–16.

(List continued on next page.)

*Primary Examiner*—Mukund J. Shah
*Assistant Examiner*—Pavanaram K Sripada
*Attorney, Agent, or Firm*—Baker Botts, L.L.P.

[57] ABSTRACT

The present invention relates to metallated or unmetallated porphyrin derivatives which have varying amphiphilic properties and which may be bonded to polymers, and to processes of their preparation. The present invention further relates to photosensitizers comprising said porphyrin derivatives, and to the use of said photosensitizers for the catalytic formation of singlet oxygen.

10 Claims, 2 Drawing Sheets

OTHER PUBLICATIONS

Muraca, Paul et al., "Comparative Assessment of Chlorine, Heat, Ozone, and UV Light for Killing Legionella pneumophila within a Model Plumbing System", *Applied and Evironmental Microbiology*, (Feb. 1987) pp. 447–453.

Harris, George D. et al., "The Influence of Photoreactivation and Water Quality on Ultraviolet Disinfection of Secondary Municipal Wastewater" *Journal WPCF*, vol. 59, No. 8 (Aug. 1987) pp. 781–787.

Martiny, Heike et al., "Use of UV–Irradiation for the Disinfection of Water I. Communication: Microbiological Investigations in Drinking Water", *Zbl. Bakt. Hyg.* B vol. 185 (1988) pp. 350–367.

Harris, Michael G. "Effects of Ultraviolet Radiation on Contact Lens Parameters" *Optometry and Vision Science*, vol. 70, No. ?, pp. 739–742 (1993).

Farooq, Shaukat et al., "Comparative Response of Mixed Cultures of Bacteria and Virus to Ozonation" *Water Res.* vol. 17, No. 7, (1983) pp. 809–812.

Kir' ianova E.V. (1996) "Optimization of Conditions of ozone water disinfection by the method of mathematical planning of an experiment" *Gig. Sanit.* 4:3–6.

Berg, J.D. et al., "Effect of Chlorine Dioxide on Selected Membrane Functions of *Escherichia coli*" *Journal of Applied Bacteriology*, vol. 60 (1986) pp. 213–220.

Grothe, Donald R. et al., "Chlorine–Induced Mortality in Fish" *Trans. Am. Fish. Soc.* No. 4 (1975) pp. 800–802.

Sobsey, Mark D. "Inactivation of Health–Related Microorganisms in Water by Disinfection Processes", *Wat. Sci. Tech.* vol. 21, No. 3 (1989) pp. 179–195.

Tuthilll, Robert W. et al., "Health Effects Among Newborns after Prenatal Exposure to $ClO_2$–Disinfected Drinking Water", *Environmental Health Perspectives*, vol. 46 (1982) pp. 39–45.

Zierler, Sally et al., "Type of Disinfectant in Drinking Water and Patterns of Mortality in Massachusetts", *Environmental Health Perspectives*, vol. 69 (1986) pp. 275–279.

Sing, Ajaib et al., "Assessment of In Vivo Revival, Growth, and Pathogenicity of *Escherichia coli* Strains after Copper– and Chlorine–Induced Injury" *Applied and Environmental Microbiology* (Oct. 1986) vol. 52, pp. 832–837.

Craun, Gunther F. "Surface Water Supplies and Health", *Journal AWWA* (Feb. 1988) pp. 40–52.

Dugan, A.M., "The products of water chlorination as inducers of gene mutations", *Tsitol. Genet.* (1996) 30:77–81.

Grayson, D.H. et al. "Polymer–Bound Porphyrides and Polymer–Bound Coordination Compounds as Converters of Solar Energy into Chemical Fuels", *Photochem., Photoelectrochem., Photobiol. Processes*, vol. 2 (1983) pp. 51–57.

Eichhorn Holger et al., "Polymer–Bound Porphyrins and Their Precursors, 11", *Macromol. Chem. Phys.* vol. 196 (1995) pp. 115–131.

Kamachi, et al., "Preparation of Polymer Containing Porphyrin Moiety. Radical Polymerization of 5–(4–Acryloyloxyphenyl)–10,15,20–Triphenylporhyrin", *J. Poly. Sci. Polym. Lett.*, 21:693–698 (1983).

Kamachi, M. et al., "Preparation and Properties of Magnetically–interacting Polymer with Cupper(II) and Vanady(II) Poporphyrins", *Chemistry Letters* (1987) pp. 2331–2334.

Kamachi, Mikiharu et al., "Synthesis of New Polymers Containing Porphyrins in Their Side Chains: Radical Polymerizations of 5–[4–(Acryloyloxy)phenyl]–10,15,20–triphenylporphyrin and 5–[4–(Methacryloyloxy)phenyl]–10,15, 20–triphenylporphyrin", *Macromolecules*, vol. 20, No. 11 (1987) pp. 2667–2669.

Kamogawa, Hiroyoshi et al., "Synthese and Reactions of Porphyrin and Metalloporphyrin Polymers", *Journal of Polymer Science*, vol. 12 (1974) pp. 2317–2325.

Heuermann, A., "Photophysical and Photosensitizing Properites of Newly Synthesized Porphyrin– and Phthalocanine–Derivatives", *Photodynamic Therapy and Biomedical Lasers*, Spinelli et al. Eds., (1992) pp. 855–859.

Wohrle, Dieter et al., "Polymer–Bound Porphyrins and Their Precursors, 10", *Makromol. Chem.* vol. 192 (1991) pp. 819–832.

Schaap, Paul A. et al., "Photooxygenations in Aqueous Solution with a Hydrophilic Polymer–Immobilized Photosensitizer", *Journal of American Chemical Society*, vol. 101 No. 14 (1979) 4016–4017.

Schaap, Paul A. et al.., "Polymer–Based Sensitizers for Photooxidations. II", *Journal of the American Chemical Society*, vol. 97, No. 13, (Jun. 25, 1975) pp. 3741–3745.

Le Guern, F. et al., "Singlet Oxygen Production Using Porphyrins Immobilized on Mineral Supports", *Bull. Soc. Chim Fr*, vol. 130 (1993) pp. 753–756.

Brkic, D. et al., "Homogeneous and Heterogeneous Photo–Oxygenation of 2,3–Dimethyl–2–Butene", *Journal of Molecular Catalysis*, vol. 3 (1977/78) pp. 173–184.

Tamagaki, Seizo et al., "Polymer–Based Sensitizers for Photochemical Reactions, Silica Gel as a Support", *J. Org. Chem.* vol. 45 (1980) pp. 1573–1576.

Mashiko, Toshio et al., "Porphyrins, Hydroporphyrins, Azaporphyrins, Phthalocyanines, Corroles, Corrins and Related Macrocycles", *Comprehensive Coord. Chem.*, vol. 2 (1987) pp. 813–898.

Lewis, T.A. et al., "Reductive Chlorination of Carbon Tetrachloride Mediated by Cationic Water–Soluble Metalloporhyrins", *Chemical Abstracts*, vol. 122, No. 12 (Mar. 20, 1995).

Ding, L. et al., "Synthesis of Water–Soluble, Catioic Functionalized Metalloporphyrins having a Cytotoxic Activity", *Chemical Abstracts*, vol. 114, NO. 20 (May 20, 1991).

Ishii, et al., (1987) "Spectrophotometric and analog derivative spectrophotometric determination of trace amounts of iron using sulfonated 5–(3,4–dihydroxyphenl)–10,15, 20–triphenylporphine", *Chem. Abstr.* 107:2110088a.

METALLATED OR UNMETALLATED PORPHYRIN DERIVATIVES HAVING AMPHIPHILIC PROPERTIES

The present invention relates to metallated or unmetallated porphyrin derivatives, and to a process for their preparation, and to their use. The present invention further relates to photosensitizers comprising said porphyrin derivatives, and to the use of said photosensitizers for initiating photochemical reactions, especially for the catalytic formation of singlet oxygen.

In particular, the invention relates to surface-charged porphyrin derivatives which are covalently bonded to a polymeric material.

Hydrophilic polymer-bound porphyrins have advantageous properties as photosensitizers. These advantages are manifest, in particular, at a polymer-water interface since these novel materials are also capable of bringing otherwise hydrophobic polymer surfaces into sufficiently intensive contact with an aqueous phase. Thus, photochemical reactions can be initiated which otherwise would fail to proceed. For the water-soluble polymer-bound porphyrins, there are other potential fields of application or operation modes than for the water-insoluble hydrophilic polymers.

Unmetallated porphyrins and also metallated porphyrins can be utilized as efficient photosensitizers. They become electronically excited when irradiated with light of sufficient energy. In a suitable combination with chemical reaction partners, the excited sensitizers can transfer either the energy or a charge to the respective reaction partner which disposes of the excess energy in subsequent reactions. A wide variety of other species is capable of serving as the energy acceptor. Also, electronically excited porphyrins may function both as donors and as acceptors to form exciplexes which can then lead to chemical reactions (T. Mashiko, D. Dolphin, Comprehensive Coord. Chem. 2, 1987, 813–898).

Of interest for technical applications are, e.g., sensitized photooxygenations, sensitized photoisomerizations, sensitized photocycloadditions and sensitized photodesulfonylations. The sensitized activation of oxygen which is present as triplet oxygen in the ground state and which may be converted to singlet oxygen when sensitized is particularly important. Singlet oxygen possesses a reactivity which is different from that of triplet oxygen. In many practical cases, the sensitizer is homogeneously dissolved in the reaction mixture. There is a disadvantage, however, in that the sensitizer must often be separated and optionally recycled with high expenditure when the reaction mixture is processed after the reaction is completed. In addition, it is often required that the product must not contain any residual sensitizer. A per se known way for reducing the expenditure is to fix the sensitizer to surfaces of support materials either physically (by adsorption) or chemically (by covalent, coordinate or electrostatic bonding). Then, after the reaction is completed, it can be readily separated, e.g., by filtration, and reused. In the literature, examples of the use of sensitizers and their heterogenization are described (A. M. Braun, M.-T. Maurette, E. Oliveros, Photochemical Technology, John Wiley & Sons, Chichester 1991; H. Böttcher (Ed.), Technical Applications of Photochemistry, Deutscher Verlag für Grundstoffindustrie 1991).

The adsorption of rose bengal to silicagel is described by S. Tamagaki et al. (J. Org. Chem. 45, 1573, 1980).

Salt formation is described, inter alia, by D. Brkic et al. (J. Mol. Catal. 3, 173, 1977/78) for rose bengal on silica gel and by F. Le Guern et al. (Bull. Soc. Chem. Fr. 130, 753, 1993) for tin porphyrins on silica gel and zeolites.

A. P. Shaap et al. (J. Am. Chem. Soc. 97, 3741, 1975) describe the reaction of Merrifield resin, a cross-linked copolymer of chloromethylstyrene and divinylbenzene, with rose bengal. This results in the formation of ester linkages between the polymer and the dye. The photosensitive polymer formed is hydrophobic and sparingly soluble in most organic solvents. An enhancement of the hydrophilicity of this polymer group is described by A. P. Shaap et al. (J. Am. Chem. Soc. 101, 4016, 1979). The use of ethylene glycol methacrylate and ethylene glycol dimethacrylate as the second component in the copolymerization of chloromethylstyrene yields more hydrophilic polymers.

D. Wöhrle et al. (Makromol. Chem. 192, 819, 1991) report on a polymer with covalently bonded zinc tetraphenylporphyrin. The material employed is zinc 5-(4-aminophenyl)-10,15,20-triphenylporphyrin. It is bonded, on one hand, to polyvinylchloromethylstyrene and, on the other hand, to activated polymethacrylate as an amide. A copolymer of poly(N-vinyl-2-pyrrolidone)methacrylic acid was also used in which the free carboxylic acid groups were methylated after the amide formation.

Heuermann et al. (Photodynamic Therapy and Biomedical Lasers 855, 1992) report the bonding of metallated 5,10,15,20-tetrahydroxyphenyl-, tetraaminophenyl- and tetracarboxyphenylporphyrins to methoxypolyethylene.

WO 93/00815 describes the physical binding of unmetallated porphyrins to polymers such as cellulose and its derivatives and to polyolefins and olefinic polymers. For the preparation of the photosensitive polymers, an extraction method and melt-extrusion are mentioned. The preparation of photosensitive polymers from dye monomers and a copolymer using unmetallated porphyrins is described. The monomers are obtained by the reaction of porphyrins which have an alcohol group with methacrylic chloride. The second monomer is methyl methacrylate. This results in a modified polymethyl methacrylate with the dye bonded through an ester linkage. The pure polymer with the dye as the alcohol component of the ester function is also described. As another chromophorous monomer, protoporphyrin dimethyl ester is used which is copolymerized with methyl methacrylate.

H. Kamogawa et al. (J. Polymer Sci. 12, 2317, 1974) report the preparation of monomers of vinyl benzyl ester with metallated and unmetallated protoporphyrin from chloromethylstyrene and the protoporphyrin. This monomer was copolymerized with N-vinylpyrrolidone to obtain water-soluble polymers. Thus, the reaction of a copolymer of chloromethylstyrene and N-vinylpyrrolidone with metallated and unmetallated porphyrins is described. As the linking group between the photosensitizer and the polymer, there is formed, on one hand, an ester linkage and, on the other hand, a Schiff's base. As the dyes, there are used, on one hand, porphyrins with carboxylic acid groups and, on the other hand, aldehyde groups.

In a second article, M. Kamachi et al. (Macromolecules 20, 2665, 1987) describe the copolymerization of unmetallated 5-(4-acryloyloxyphenyl)-10,15,20-triphenylporphyrin and 5-(4-methacryloyloxyphenyl)-10,15,20-triphenylporphyrin with methyl methacrylate. The polymer metallated with iron, vanadium or cobalt was obtained by subsequent metallation or through the use of metallated monomers (Chem. Letters 2331, 1987).

M. Kamachi et al. (J. Polymer Sci. 21, 693, 1983) describes the polymerization of 5-(4-acryloyloxyphenyl)-10,15,20-triphenylporphyrin. The use of the metallated monomer has also been described. The polymer obtained is insoluble in ethanol, acetone, water and hexane. The unmetallated polymer could be subsequently metallated with copper.

H. Eichhorn et al. (Macromol. Chem. Phys. 196, 115, 1995) describe the preparation of monomers based on unmetallated 5,10,15,20-tetraphenylporphyrin. Groups containing double bonds were attached to the four para positions of the phenyl rings. Thus, methacryloyl residues were attached through the phenol group. The copolymerization with styrene yielded polymers which contain the porphyrin as a junction point.

D. H. Grayson et al. (Sol. Chem. R&D Eur. Community, Ser. D., 2, 51, 1983) describe a polymer of zinc tetraphenylporphyrin bonded to polyvinylpyridine.

In DE 3836759 A1 and DE 3924815 A1, W. Wolters describes the use of phthalocyanins and diazotized β-naphthol, physically bound, which is fixed with a binder as a catalyst for the activation of oxygen. As the binders, there are used, on one hand, acrylic esters and/or methacrylic esters and, on the other hand, polyurethans.

In the prior art, a number of processes for the disinfection and/or detoxification of water and/or water-containing environments and of objects are known.

The well-known chlorination may be mentioned first. See, for example, Dugan, A. M., 1996, The products of water chlorination as inducers of gene mutations, Tsitol. Genet. 30: 76–81; Craun, G. F., 1988, Surface water supplies and health, J. Am. Water Works Assoc. 80: 40–42; Singh, A., Yeager, R., and McFeters, G. A., 1986a, Assessment of in vivo revival, growth and pathogenicity of *E. coli* strains after copper- and chlorine-induced injury, Appl. Environ. Microbiol. 52: 832–837; Zierler, S., Danly, R. A., Feingold, L., 1986, Type of disinfectant in drinking water and patterns of mortality in Massachusetts, Environ. Health Perspect 69: 275–279; Jolley, R. L., Brungs, W. A., and Cummings, R. B., Eds., 1985, Water chlorination: Chemistry, Environmental Impact, and Health Effects, Lewis Pubs., Chelsea, M I; Tuthill, R. W., Giusti, R. A., Moore, G. S., Calabrese, E. J., 1982, Health effects among newborns after prenatal exposure to $ClO_2$-disinfected drinking water. Environ. Health Perspect 46: 39–45. The essential drawback of chlorination resides in the high costs caused by the permanent consumption of chemicals. In addition, side products are formed which are known to be toxic, for example, cancerogenic or mutagenic, such as trihalomethanes and other organic chemical compounds. Further, the offensive smell and taste adversely affect the water quality. Some microorganisms are known to be resistant to chlorine so that a supplementary treatment is often to follow. Many microorganisms, although hindered by chlorine in their reproducibility, are nevertheless capable of producing enterotoxins.

Besides chlorination, chloroamination is known, for example, from Sobsey, M. D., 1989, Inactivation of health-related microorganisms in water by disinfection processes, Water Sci. Technol. 21: 179–195; Groethe, D. R., and Eaton, J. G., 1975, Chlorine induced mortality in fish. Trans. Am. Fish Soc. 104: 800–805. In this case also, an essential drawback resides in the high costs caused by the permanent consumption of chemicals. Although no trihalomethanes are formed in this case, chloroamination is less effective than chlorination. An offensive taste in the detoxification and disinfection of water can be observed here as well. Many organisms are resistant to chloroamination so that additional measures are required here as well. It has to be pointed out, in particular, that chloroamination is very nocuous to aquatic systems. Mutagenic and cancerogenic effects on humans are suspected.

The treatment of water with chlorine dioxide is known, for example, from Berg, J. D., Roberts, P. V., and Martin, A., 1986, Effect of chlorine dioxide on selected Membrane functions of *Escherichia coli*, J. Appl. Bacteriol. 60: 213–220. Chlorine dioxide always has to be freshly prepared before use since there is no possibility of storing it. Accordingly, this process is significantly more expensive than the treatment of water with chlorine. The formation of trihalomethanes and chloroamine is not to be feared, but the side products chlorite and chlorate lead to methemoglobinemia because they can have an impact on the hemoglobin in humans.

Ozonization according to Kir'ianova, E. V., 1996, Optimization of conditions of ozone water disinfection by the method of mathematical planning of an experiment, Gig. Sanit. 4: 3–6; Farooq, S., Akhlaque, p. 1983, Comparative response of mixed cultures of bacteria and viruses to ozonisation, Water Res. 17: 809–812, is very tedious with respect to construction, operation and maintenance. Since ozone is not a stable compound, the water mostly has to be additionally admixed with chlorine for a prolonged disinfectant effect. Some microorganisms are resistant to ozone as well. As side products, aldehydes are frequently formed which may have a mutagenic effect.

Another process for the treatment of water and/or water-containing environments is irradiation with ultraviolet light. See, for example, Harris, M. G., Buttino, L. M., Chang, J. C., Wan, M., 1993, Effects of ultraviolet radiation on contact lense parameters, Optom. Vis. Sci. 70: 739–742; Martiny, H., Wlodavezyk, K., Harms, G., Ruden, H., 1988., The use of UV rays for the disinfection of water. I. Microbiologic studies of drinking water. Zentralbl. Bakteriol. Mikrobiol. Hag. (B), 185: 350–367;,Harris, G. V., Adams, V. D., Sorensen, D. L., and Dupont, R. R., 1987, The influence of photoreactivation and water quality on ultraviolet disinfection of secondary municipal wastewater. J. Water Pollut. Control Fed. 59: 781–787; Muraca, P., Stout, J. E., Yu, V. L., 1987, Comparative assessment of chlorine, heat, ozone, an UV-light for killing Legionella pneumophila within a model plumbing system, Appl. Environ. Microbiol. 53: 447–453; Myhrstadt, J. A., 1979, Disinfection of sewage water by ultraviolet irradiation, NIPH, Ann. 2: 11–16. Since no active substances remain in the treated water, subsequent chlorination is necessary as a rule, which again gives rise to additional costs. Depending on the turbidity, oxygen content, the content and type of solubilized particles and chemical contaminations of the water to be treated, the dosage determination is very problematic. There is a possibility of photoreactivation; therefore, it must be ensured that the water is not stored in the light during or after UV irradiation.

Because of biofilm formation on the lamp, continuous monitoring and careful cleaning of the lamp, whether chemically, mechanically or with ultrasound, is important which causes additional maintenance costs. When the lamp is operated, it is to be taken care that persons are sufficiently safe since UV light is known to have a mutagenic and cancerogenic effect. UV light causes a number of materials to fatigue. UV light is known to promote the formation of ozone which is hazardous to the health.

From Ahlstrom, S. B., and Lessel, T., 1986, Irradiation of municipal sludge for pathogen control, in: Control of Sludge Pathogens, C. A. Sorber, Ed., Water Pollution Control Federation, Washington D.C., the treatment of water with gamma radiation and high-energy electron radiation is known. The plants employed are very expensive and complicated which involve a high safety risk. The effect can be improved if heat or oxygen is additionally supplied, which further increases the costs, however.

From Polyzois, G. L., Zissis, A. J., Yannikakis, S. A., 1995, The effect of glutaraldehyde and microwave disinfection on some properties of denture resin, Int. J. Prosthodont. 8: 150–154; and Niederwohrmeier, B., Bohm, R., Strauch, D., 1935, Microwave treatment as an alternative pasteurization process for the disinfection of sewage sludge: Experiments with the treatment of liquid manure, pp. 135–147, in: Inactivation of Microorganisms in Sewage Sludge by Stabilisation Processes, D. Strauch, A. H. Havelaar, and O. L. L'Hermite, Eds., Elsevier Applied Science, London, the treatment of water with microwave radiation is known. This measure is very expensive too since complicated plants and safety measures are required. The additional supply of heat further increases the costs, the effect of the radiation being improved, however. For large volumes, however, microwave irradiation is very problematic since optimum mixing should be ensured.

From Joyce, T. M., McGuigan, K. G., Elmore-Meegan, M., Conroy, R. M., Inactivation of fecal bacteria in drinking water by solar heating, Appl. Environ. Microbiol. 62: 399–402, and Fuhrmann, H., Floerke, I., Bohm, K. H., 1986, The problem of heat activation of bacterial spores after disinfection with regard to an aerosol method of decontaminating equipment and rooms, Zentralbl. Bakteriol. Mikrobiol. Hyg. (B) 182: 515–524, heat sterilization is known. This is also associated with a high expenditure of energy, while complete inactivation of all organisms is not always achieved. In addition, heat sterilization is unsuitable for large quantities.

Hegna, I. K., Clausen, O. G., 1988, An investigation of the bactericidal and fungicidal effects of certain disinfectants by use of capacity test, Ann. Inst. Pasteur, Microbiol. 139: 473–483; LeChevallier, M. W., and McFeters, G. A., 1985b, Ennumerating injured coliforms in drinking water, J. Am. Water Works Assoc. 77: 81–87; Conn, H., Langer, R., 1981, Iodine disinfection of hydrophilic contact lenses, Ann. Ophthalmol. 13: 361–364, describe other kinds of additions of chemicals and metals. These processes too are characterized by a continuous consumption of substances, by a tedious recovery of the substances, by injuries to health from the added substances, for example, formaldehyde, phenol and glutaraldehyde. In many cases, injuries to health from the generated side products cannot be ruled out.

Archer, A., Fischer, E., Zellingher, R., Manor, Y., 1990, Photochemical disinfection of effluents-pilot plant studies, Wat. Res. 24: 837–843; Dahl, T. A., Midden, W. R., Neckers, D. C., 1988, Comparison of photodynamic action by Rose Bengal in gram-positive and gram-negative bacteria, Photochem. Photobiol. Vol. 48 No. 5: 607–612; Archer, A. J., Juven, B. J., 1976, Destruction of Coliforms in Water and Sewage Water by Dye-Sensitized Photooxidation, Appl. Environ. Microbiol. 33: 1019–1022, describe photodynamic disinfection with dyes dissolved in water. This also requires a continuous consumption of substances and involves problems with the recovery of the substances, for example, methylene blue or rose bengal.

Filtration which is described, for example, by Dorau, W., 1996, Mikrofiltration als Schlußreinigung bei der Abwasserreinigung, Notwendigkeit, verfahrenstechnische Einbindung, Kosten, Gewässerschutz-Wasser-Abwasser 152: 51/1–28, and Kolega, M., Grohmann, G. S., Chiew, R. F., Day, A. W., 1991, Disinfection and clarification of treated sewage by advanced microfiltration, Water Sci. Technol. 23: 1609–1618, is a tedious measure for the treatment of water. The filters very readily clog so that a high maintenance expenditure is required which necessitates regular mechanical and chemical cleaning of the plant.

The photosensitive polymers based on polymethyl methacrylate known to date are either water-soluble or insoluble. A polymer with hydrophilic character which is nevertheless water-insoluble is not known. The bound porphyrins based on metallated and unmetallated tetraphenylporphyrin in the known polymers do not possess any groups in the para position of the phenyl groups which bear a positive or negative charge. The access to polymers based on polymethyl methacrylate and tetraphenylporphyrins has been described only via the monomers.

In a first embodiment, the above object of the present invention is achieved by metallated or unmetallated porphyrin derivatives of general formula I

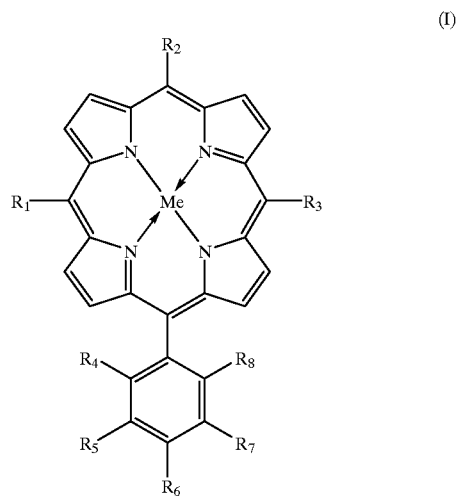

wherein $R_1$, $R_2$ and $R_3$ respectively represent hydrogen; alkyl, aryl, aralkyl or alkaryl, alkyl-, aryl-, aralkyl- or alkarylsulfonate, or pyridine-N-alkyl, -aryl, -alkaryl or -aralkyl each having from 1 to 8 carbon atoms, with the proviso that at least one of $R_1$, $R_2$ or $R_3$ is not hydrogen, alkyl, aryl, aralkyl or alkaryl;

$R_4$, $R_5$, $R_6$, $R_7$ and $R_8$ respectively represent hydrogen, a hydroxy group, or a polymer residue derived from polyesters, polymethyl methacrylates, polymethacrylic acid, polyacrylic acid and its esters, polymethacrylamides, polyacetals, polyimides and/or polyamides, and their respective monomer units, with the proviso that at least one of $R_4$, $R_5$, $R_6$, $R_7$ or $R_8$ is not hydrogen; and Me represents a metal cation or saturation with hydrogen atoms. In particular, Me represents a metal cation having a half-occupied or completely occupied d electron shell, or aluminum.

Surprisingly, it has been found that the optionally hydrophilic porphyrin derivatives of general formula I which are provided for the first time are efficient sensitizers which, in addition, can be readily or are already covalently bound to polymers. By modifying the substituents $R_1$, $R_2$ and $R_3$ with polar groups, the hydrophilicity of these polymers can be controlled within a broad range so that, on one hand, hydrophobic polymers (i.e. containing no polar groups) and, on the other hand, even water-soluble polymers (high content of polar groups) can be prepared. Between these two extremes, there are hydrophilic and yet water-insoluble polymers. In addition, the water-solubility can be controlled through the degree of polymerization of the basic polymer.

In a particularly preferred embodiment of the present invention, the metallated or unmetallated porphyrin derivatives of general formula I are characterized in that $R_4$, $R_5$, $R_7$ and $R_8$ each represent hydrogen, and $R_6$ represents a hydroxy group. Those compounds preferably serve as the starting materials for the reaction with monomer units or polymer units for the covalent fixation of the porphyrin derivatives, in particular, by the transesterification of existing ester groups.

Another aspect, of the invention is the introduction of sulfonic acid groups in the alkyl, aryl, alkaryl or aralkyl groups of the porphyrin derivative. The degree of sulfonation can be controlled by the addition of the sulfonating agent whereby the hydrophilic character of the polymer can be changed. The sulfonation can be performed prior to the preparation of the monomers, or after the preparation of the polymers.

Another aspect of the invention is the alkylation of the pyridine groups of the porphyrin derivatives. The degree of alkylation can be controlled by the addition of the alkylating agent. The alkylation can be performed prior to the preparation of the monomers, or after the preparation of the polymers. Alkyl derivatives having from 1 to 8 carbon atoms are particularly suitable for alkylation.

Another aspect of the invention is the introduction of metals, especially those having a half-filled d electron shell, after the unmetallated photosensitive polymer is available. It is particularly preferred that the porphyrin derivatives contain zinc as the central cation.

A special aspect of the invention is the preparation of porphyrin-containing polymethyl methacrylates via the transesterification of the existing ester groups with 5-(4-hydroxyphenyl)-10,15,20-triarylporphyrin derivatives. Such porphyrins may be metallated or unmetallated.

Another preferred embodiment of the present invention consists in a process for the preparation of porphyrin derivatives of general formula I by reacting porphyrin derivatives of general formula II

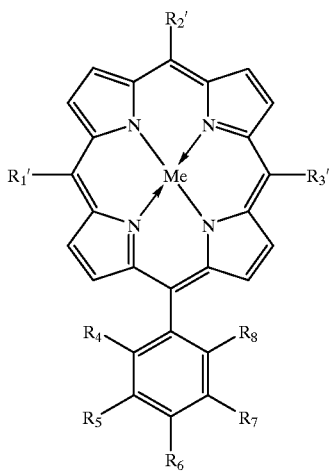

(II)

wherein $R_{1'}$, $R_{2'}$ and $R_{3'}$ respectively represent hydrogen, alkyl, aryl, aralkyl or alkaryl having from 1 to 8 carbon atoms, with the proviso that at least one of $R_{1'}$, $R_{2'}$ or $R_{3'}$ is not hydrogen; and Me, $R_4$, $R_5$, $R_6$, $R_7$ and $R_8$ are as defined above;

with a sulfonating agent, optionally followed by a subsequent metallation.

It is particularly preferred according to the present invention to employ chlorosulfonic acid or concentrated sulfuric acid as said sulfonating agent according to per se known methods.

Another process for the preparation of porphyrin derivatives of general formula I comprises reacting about four parts of pyrrole, about one to three parts of pyridinecarboxyaldehyde and about one part of benzaldehyde followed by N-alkylation and optionally metallation.

Another preferred embodiment of the process according to the present invention for the preparation of porphyrin derivatives comprises reacting porphyrins of general formula I wherein $R_1$, $R_2$, $R_3$ and Me are as defined above, $R_4$, $R_5$, $R_6$, $R_7$ and/or $R_8$ represent hydrogen or a hydroxy group, with the proviso that at least one of $R_4$, $R_5$, $R_6$, $R_7$ or $R_8$ represents a hydroxy group;

with polyesters, polymethyl methacrylates, polymethacrylic acid, polyacrylic acid and its esters, polymethacrylamides, polyacetals, polyimides and/or polyamides, or their respective monomer units.

It is particularly preferred according to the present invention to react the above mentioned porphyrin derivatives with polymethyl methacrylate and/or polycarbonates.

Another aspect of the invention is the preparation of porphyrin derivatives via the copolymerization of methacrylate with metallated and unmetallated monomers of the esters of methacrylic acid or acrylic acid and 5-(4-hydroxyphenyl)-10,15,20-triarylporphyrin derivatives. The latter monomers may contain sulfonic acid groups or pyridinium salts. The photosensitizers thus obtained are attached to the polymer skeleton through a covalent bond and project from the polymer. They are not junction points embedded within the polymer.

Another embodiment of the present invention relates to photosensitizers containing at least one porphyrin derivative of general formula I in an amount of from 0.1 to 10% by weight. Said porphyrin derivative of general formula I is present in a polymer matrix in a covalently bonded or non-covalently bound form. Particularly preferred according to the present invention is covalent fixing of the porphyrins in the support material.

As polymeric support materials, PMMA and polycarbonates are primarily interesting for technical applications because they have advantageous properties: being inexpensive, mechanically stable, weather-resistant, light-resistant, transparent in the region of light required for the excitation of the sensitizers.

According to the invention, the polymer matrix may preferably consist of fibers, granules, non-woven, woven or knitted fabrics or bodies with an arbitrary shape, for example, membranes.

Another aspect of the invention is the use of the photosensitive monomers and polymers as sensitizers for photochemical reactions. The prepared monomers and polymers are suitable for the transfer of energy taken up from light to chemical substances.

In the prior art (WO 93/00815), there have been attempts to fix porphyrins to polymers. The procedure was to dye regenerated cellulose with TRPyP; cytotoxicity was observed.

For applications in which long-term stability of the sensitizers fixed to polymers in aqueous environments is required, it is disadvantageous to bond the porphyrin derivatives to cellulose since cellulose will slowly hydrolyze. This drawback does not exist in the case of covalent bonding to PMMA. Although it has been found in the prior art that cell growth is inhibited upon direct contact with bacterial cultures, the porphyrins employed are characterized by being fourfold symmetrically substituted, having no central atom and possess positively charged 4-alkylpyridines.

However, in our own experiments in the frame of the present invention, it has been found surprising that the formation of singlet oxygen could not be observed upon the irradiation of 5-(4-hydroxyphenyl)-10,15,20-triphenylporphyrin fixed to PMMA which was in direct contact with an air-saturated aqueous phase. This difference from the prior art in which this dye was also used can possibly be accounted for in that a direct contact with the respective bacterial culture was ensured whereas in the experiments according to the invention, a diffusion barrier at the polymer-water interface had to be overcome.

One important difference between the present invention and TRPyP derivatives of the prior art is that they have a symmetric structure and lack a functional group for covalent bonding. According to the invention, unsymmetrical porphyrins are synthesized which are, in particular, fixed to a support material via an ester function.

The use of the known fourfold acrylated tetra-5,10,15,20-(4-hydroxyphenyl)porphyrin as a comonomer in the preparation of photosensitive PMMA incorporates the dye in the polymer structure as a cross-link. Thus, only a few dye units will get to the surface of the polymer and thus be photosensitive. The yield of singlet oxygen, based on the number of dye molecules, is significantly reduced. In the porphyrin derivatives according to the invention, the dye units are freely accessible because they are bound to the support material only through one functional group.

According to experiments of the present invention, the use of the known 5-(4-hydroxyphenyl)-10,15,20-triphenylporphyrin fixed to PMMA in aqueous systems does not induce the formation of singlet oxygen. In contrast, the dyes prepared according to the invention have higher hydrophilicity and are thus capable, inter alia, of producing good singlet oxygen formation rates. The per se known process for the preparation of the polymer via free-radical polymerization takes 5 to 6 days, or 2 days in the copolymerization with styrene. The preferred process according to the invention, via transesterification, yields a product within a few hours.

According to the invention, the activation of oxygen nevertheless succeeded through a modification of the bound porphyrins. The modification consists in attaching negatively or positively charged groups to the porphyrin skeleton. With that strategy, porphyrin derivatives of general formula I were first prepared which contain as common features:
  charge
  linking Another object of the present invention has been to improve the treatment, in particular, of water or water-containing environments by the irradiation with actinic, i.e., visible, light. Further, it has been the object of the present invention to provide articles or containers for the disinfection and/or detoxification of objects in oxygen and especially water and/or water-containing environments.

In one embodiment, the above object is achieved by the use of the above mentioned porphyrins for the detoxification and/or disinfection of oxygen and especially water or water-containing environments by irradiation with actinic light.

The particular advantages of the present invention are a low energy expenditure for operating the plant. Disinfection and decontamination can be effected in one process step. Due to the binding to a polymeric support material, problems of recovery do not occur in the present invention. The porphyrins bound to the polymer remain in the system so that no permanent costs arise from the continuous addition of compounds. No toxic side products or dyes are formed, neither do any decomposition products of the metallated and/or unmetallated porphyrins bound to the polymer occur.

Since the substance is not toxic, no additional safety measures are required. Thus, the process according to the invention of using metallated and/or unmetallated porphyrins bound to a polymer is also suitable for the cleaning of large volumes. In regions abundant with sun, no additional light sources are necessary. In combination with small mobile units, the principle underlying the invention can also be employed in secluded areas.

It has been surprising, however, that the porphyrins bound to a polymer will swell upon contact with water or water-containing environments and thus advantageously form singlet oxygen upon irradiation with actinic (visible) light in this case as well.

It is particularly preferred according to the present invention to employ the porphyrins for the treatment of water or water-containing environments in sewage treatment plants. For the after-purification of contaminated water, the latter can be processed such that the water can be recycled as service water within the plant. This possibility to recycle, in principle, not only exists in communal and industrial sewage (waste water) treatment plants, but also, for example, in the food industry where fruits and vegetables are washed for canning. In the textile industry, especially in tanneries and whereever large amounts of water are obtained which can be recycled to the internal service water cycle in this way, thus significantly reducing the costs for water and waste water, treatment of the water by means of the present invention is possible. The present invention is also suitable, in particular, for the treatment of washing/bathing and showering water of large hotels or camping sites. A permanent disinfection of swimming pools is also possible by means of the present invention whereby the chlorine consumption and thus the impact on the environment and health as well as the operating costs can be significantly reduced.

In outer space, for example, treatment of the service water is possible in transparent tanks.

In addition, the process according to the invention can be employed for the purification of exhaust air or recirculated air, especially of air from cattle sheds, or for deodorizing exhaust air or recirculated air streams in buildings, for example, department stores.

In a particularly preferred embodiment of the present invention, the above mentioned porphyrins are employed in the form of flat-bed reactors or bubble columns.

Another preferred embodiment of the present invention consists in using the above mentioned porphyrins as stationary structures, especially sheets of solid material or coated sheets and as granules, powders, membranes or filters.

In addition to the above mentioned aqueous systems which can be detoxificated or decontaminated by means of the present invention, it is possible, in a further embodiment of the present invention, to disinfect and/or detoxificate all kinds of objects with the above mentioned porphyrins. Therefore, it is particularly preferred according to the present invention to place said objects in an aqueous or water-containing environment and to contact them with the porphyrins in this way.

Thus, one particular embodiment of the present invention is to provide containers or articles for the detoxification and/or disinfection of water or water-containing environments. According to the present invention, the mentioned containers or articles comprise surface regions made of porphyrins bound to a polymer. Thus, per se known containers or articles are prepared containing the porphyrins bound to a polymer at least in parts of their surface area.

Thus, for example, the containers described above may comprise purification devices for contact lenses, dental prostheses or dental regulatory devices. Thus, another embodiment of the present invention consists of articles comprising antibacterial coatings of surfaces in medical engineering, said surfaces containing metallated or unmetallated porphyrin derivatives bound to a polymer.

The use of the porphyrins for the purification of water or air according to the invention relies on the production of singlet oxygen. The use of this agent is described in several publications. Thus, for example, in Archer et al., loc. cit.; in Banks, J. G., Board, R. G., Carter, J., and Dodge, A. D. (1984), The cytotoxic and photodynamic inactivation of micro-organisms by Rose Bengal, J. Appl. Bacteriol., 58, 391–400; Dahl, T. A., Midden, W. R., and Hartman, P. E. (1987), Pure singlet oxygen cytotoxicity for Bacteria, Photochem. Photobiol. 46, 345–352.

A general survey of the reactions which can be performed with singlet oxygen is described in Houben Weyl, Methoden der organischen Chemie, Photochemie Band II, Georg Thieme Verlag Stuttgart, 1975, p. 1465. As classes of chemical substances, it mentiones alkenes, aromatics, heteroaromatics, nitrogen, sulfur and phosphorus compounds and others. They can be converted to a higher oxidized derivative and thus prepared for a biological clarification of the water. In the case of the sulfur compounds, the higher oxidized materials possess a reduced inherent smell, and thus a desodorizing effect can be observed here.

It can be derived therefrom that a dye which produces singlet oxygen can be employed, in principle, in water as a sensitizer for the water purification.

The reactivity of singlet oxygen in the gas phase has been demonstrated in various publications, such as, for example, in Eisenberg, Walter C., DeSilva, Mutha, Journal, TELEAY, Tetrahedron Lett., EN, 31, 41, 1990, 5857–5860, "Atmospheric gas phase generation of singlet oxygen by homogeneous photosensitization"; Borisov, A. V., Tsivenko, V. I., Myasinkov, I. A., Venediktor, E. A., Journal RJPCAR, Russ. J. Phys. Chem. (Engl. Transl.) EN, 64, 6, 1990, 922–924, "Photostimulated formation and emission of singlet oxygen from the surface of metallo-tetraphenylporphins adsorbed on silica", and Borisov, A. V., Tsivenko, V. I., Myasnikov, I. A., Journal, RJPCAR, Russ. J. Phys. Chem. (Engl. Transl.), EN, 66, 2, 1992, 307–308, "Photostimulated emission of singlet oxygen molecules into the gas phase from tetra(m-butoxyphenyl)porphin adsorbed on $SiO_2$". For the treatment of exhaust air and waste gases, the following processes are known:

1. Separation of gaseous substances by absorption, condensation, membrane permeation and dry sorption. Its drawback is the consumption of chemical auxiliary agents, such as active charcoal, lime, etc.
2. Degradation of dioxins and furanes in waste gases with hydrogen peroxide.
   Its drawback is the consumption of hydrogen peroxide.
3. Separation of gaseous harmful substances by catalytic reactions, such as oxidation, reduction and decomposition reactions. Noble metal catalysts, heavy metal catalysts and oxidic catalysts are employed. Its drawback lies in abrasion which may lead to poisoning of the catalysts. The catalysts are in part only effective at elevated temperatures. For the oxidation catalysts, the more expensive platinum metal is mostly employed. Expensive ozone is employed for the disinfection of exhaust air. The excess must be destroyed again.
4. Separation of gaseous harmful substances by biological reactions: bioscrubbers (absorption in a liquid to which microorganisms have been added), biofilters (both adsorption to a solid surface and absorption in a liquid) and biomembrane filter methods.

The methods have been taken from the Handbuch des Umweltschutzes und der Umweltschutztechnik, Vol. 3: Additiver Umweltschutz: Behandlung von Abluft und Abgasen, H. Bauer (ed.), Springer Verlag, Berlin, 1996.

All methods which are employed, for example, in the preparation of articles made of PMMA can be used according to the invention as well as long as the temperatures are below 200° C.

Therefore, another embodiment of the invention comprises the use of photosensitizers according to the present invention for the formation of singlet oxygen from triplet oxygen by the action of visible light, especially for the purification of contaminated liquids, for example, water. Singlet oxygen can also be employed as an oxidizing agent for the treatment of exhaust air and waste gases. As contemplated by the invention, the above-mentioned porphyrins are exposed to actinic light in amounts sufficient for the treatment of said air and gases. For example, the present invention may be employed in combination with gas scrubbers in which loaded washings are obtained.

One particular embodiment of the invention is characterized in that metallation, sulfonation or alkylation may be performed only with the finished modified polymer. This involves the possibility, in particular, to control the respective degrees more precisely.

EXAMPLES

Example 1

5-(4-Hydroxyphenyl)-10,15,20-tris(4-sulfonatophenyl)porphyrin

In 10 ml of concentrated sulfuric acid, 500 mg of 5-(4-hydroxyphenyl)-10,15,20-triphenylporphyrin was dissolved. The solution was stirred at a temperature of 110° C. for 10 h. After cooling and neutralization, the precipitated product was separated. Purification was performed by column chromatography on silica gel with acetone/petroleum ether as the eluent.

Example 2

Zinc(II) 5-(4-hydroxyphenyl)-10,15,20-tris(4-sulfonatophenyl)porphyrin

A mixture of 1 g of 5-(4-hydroxyphenyl)-10,15,20-tris(4-sulfonatophenyl)porphyrin and 54.5 mg of zinc acetate was dissolved in 250 ml of acetic acid and 50 ml of chloroform, and the solution was heated to reflux. The product which precipitated upon cooling was purified by column chromatography on silica gel with acetone/petroleum ether as the eluent.

To a mixture of 1 g of zinc 5-(4-hydroxyphenyl)-10,15,20-triphenylporphyrin and chloroform, there was added 60 μl of chlorosulfonic acid dissolved in 10 ml of chloroform at 0° C. After 12 h, the solution was poured on ice, and the organic phase was separated. Evaporation of the solvent yielded the product.

Example 3

5-(4-Hydroxyphenyl)-10,15,20-tris(N-methyl-4-pyridinium)porphyrin

A mixture of four parts of pyrrole, three parts of pyridine-4-carboxyaldehyde and one part of benzaldehyde in propionic acid was heated for 1 h. The solvent was evaporated, and the residue washed with DMF and ether. For further purification, the product formed was processed by means of column chromatography on silica gel with acetone/petroleum ether as the eluent. Methylation was performed with methyl p-toluenesulfonate.

Example 4

Zinc (II) 5-(4-hydroxyphenyl) -10,15,20-tris(N-methyl-4-pyridinium) porphyrin

A mixture of 1 g of 5-(4-hydroxyphenyl)-10,15,20-tris(N-methyl-4-pyridinium)porphyrin and 54.5 mg of zinc acetate was dissolved in 250 ml of acetic acid and 50 ml of chloroform, and the solution was heated to reflux. The product which precipitated upon cooling was purified by column chromatography on silica gel with acetone/petroleum ether as the eluent.

A mixture of 1 g of zinc 5-(4-hydroxyphenyl)-10,15,20-tris(pyridinium)porphyrin was reacted with 10 g of methyl p-toluenesulfonate in DMF with heating. After evaporation of the solvent, the resulting product could be recrystallized from acetone.

Example 5

5-(4-Methacryloyloxyphenyl)-10,15,20-tripyridiniumporphyrin

In 20 ml of DMF, 1 g of 5-(4-hydroxyphenyl)-10,15,20-tris(pyridinium)porphyrin was dissolved, and 128 μl of methacrylic acid was added in the presence of 200 μl of triethylamine. After completion of the reaction, the solvent was removed, the photosensitive monomer was taken up in ether and filtrated. After evaporating the ether, the pure monomer was collected.

Example 6

Zinc(II) 5-(4-hydroxyphenyl)-10,15,20-tris(4-sulfonatophenyl)porphyrin (fixed)

a) A mixture of 200 mg of polymethyl methacrylate (PMMA) and 280 mg of zinc(II) 5-(4-hydroxyphenyl)-10,15,20-tris(4-sulfonatophenyl)porphyrin in toluene was heated in the presence of p-toluenesulfonic acid. The polymer thus underwent transesterification. The dye was completely fixed by repeatedly distilling off the toluene.

b) 74 mg of zinc(II) 5-(4-methacryloyloxyphenyl)-10,15,20-tris(4-sulfonatophenyl)porphyrin was dissolved in DMF together with 10 ml of methyl methacrylate. Polymerization was initiated with azobis (isobutyronitrile) (AIBN). Removing the solvent yielded the desired polymer as a red powder.

c) 10 g of the zinc(II) 5-(4-hydroxyphenyl)-10,15,20-triphenylporphyrin fixed to PMMA was dissolved in chloroform, and 6 ml of chlorosulfonic acid was added. Neutralizing and evaporating the solvent yielded the desired polymer.

d) 10 g of the 5-(4-hydroxyphenyl)-10,15,20-tris(4-sulfonatophenyl)porphyrin fixed to PMMA was dissolved in 200 ml of chloroform, and zinc acetate was added. After heating and evaporating the solvent, the desired polymer was isolated.

Example 7

Singlet Oxygen Production of the Dyes (Porphyrin Derivatives)

The ability of the dyes to produce singlet oxygen was tested by a simple test. An aqueous solution containing an excess of imidazole (0.01 mol/l) and a concentration of $3 \times 10^{-5}$ mol/l of p-nitrosodimethylaniline (RNO) was saturated with air or oxygen under continuous stirring during the measurement. Imidazole acted as an acceptor for singlet oxygen, and the intermediary endoperoxide induced bleaching of the RNO which was monitored by spectrophotometry at a wavelength of 440 nm.

Zinc(II) 5-(4-hydroxyphenyl)-10,15,20-tris(4-sulfonatophenyl)porphyrin (2 ppm) was added to 10 ml of this RNO solution, which was then irradiated. The singlet oxygen formation rate was determined to be $8.8 \times 10^{-8}$ mol/l/s. For comparison, rose bengal had a value of $2.6 \times 10^{-8}$ mol/l/s.

The polymer of Example 6 c) in suspension was subjected to the mentioned test and irradiated. After scaling, a value of $3.0 \times 10^{-8}$ mol/l/s was determined.

Example 8

Experiment for the Determination of Singlet Oxygen Production Rates of Different Sensitizers in Water In the presence of imidazole or furfuryl alcohol as the acceptor, p-nitrosodimethylaniline (RNO) was bleached upon irradiation with polychromatic light. This reaction had been used by F. Le Guern, C. Bied-Charreton, J. Faure, Bull. Soc. Chem. Fr. 130, 753 (1993), to determine singlet oxygen production rates of sensitizers.

The design of the irradiating device employed was as follows:

A solution containing an excess of imidazole and a known concentration of nitrosodimethylaniline (RNO) was filled in a Petri dish. The solution was permanently saturated with oxygen. Upon adding the dye to be examined and irradiating with a constant light source, the bleaching of the RNO could be followed spectroscopically. The decrease of RNO concentration was plotted against time. The slope of the resulting straight line was a measure of the singlet oxygen production rate.

For comparison, the results are set forth together with those for the known sensitizer rose bengal.

Thus, the following singlet oxygen production rates were determined for different sensitizers:

| Dye | Singlet oxygen production rate, $\Delta c(^1O_2)/\Delta t$ [(mol/1)/s] |
| --- | --- |
| Rose bengal* | $1.2 \cdot 10^{-8}$ |
| Zinc(II) 5-(4-hydroxyphenyl)-10,15,20-tris(4-sulfonatophenyl)-porphyrin, bound to polymethyl methacrylate** | $8.8 \cdot 10^{-8}$ |
| Zinc(II) 5-(4-hydroxyphenyl)-10,15,20-tris(4-methylpyridino)-porphyrin, bound to polymethyl methacrylate*** | $1.8 \cdot 10^{-8}$ |

*Comparison, homogeneously dissolved
**obtainable according to Example 6
***obtainable according to Example 4

Example 9

Detection of the Decomposition of Chemical Substances by Means of a Porphyrin Polymer For the decomposition of chemical substances, a falling film reactor was prepared. In the latter, both homogeneously dissolved sensitizers and PMMA sheets made from photosensitive materials can, be examined. FIG. 1 schematically shows its design.

The pesticide phosphoric acid tributyl thioester (DEF), which occurs in some countries as a contaminant in the ground water, was employed as the test substance. The detection of the substance was effected by means of GC using concentration techniques.

The following results were obtained wherein $C_i$ represents the initial concentration, and $C_f$ represents the final concentration.

| Dye | $C_i$ (DEF) [ppm] | $C_f$ (DEF) [ppm] |
|---|---|---|
| Rose Bengal* | 3.2 | 0.23 |
| Zinc(II) 5-(4-hydroxyphenyl)-10,15,20-tris(4-methylpyridino)porphyrin, bound to polymethyl methacrylate*** | 3.04 | 0.77 |

*Comparison, homogeneously dissolved
***obtainable according to Example 4

Example 10

Detection of Disinfection by Means of a Porphyrin Polymer

The following apparatus was employed for the disinfection experiments.

A Polytec 1000 W xenon lamp was used as the light source. In order to filter off the UV fraction emitted by the lamp, the samples were covered with 3 mm thick Pyrex glass. The spectrum of the lamp below the Pyrex glass was examined and was essentially identical with that of the sun. In order to be able to control or keep constant the temperature during the experiment, the samples were irradiated in a cooling element and agitated with a magnetic stirrer during irradiation.

BRIEF DESCRIPTION OF THE DRAWINGS

The design of the irradiating unit is schematically shown in FIG. 2.

For the experiments with dyes, the cells of *D. radiodurans* were selected as the object to be examined. The experiments yielded the survival curves represented in FIG. 3.

Example 11

Figure 1:
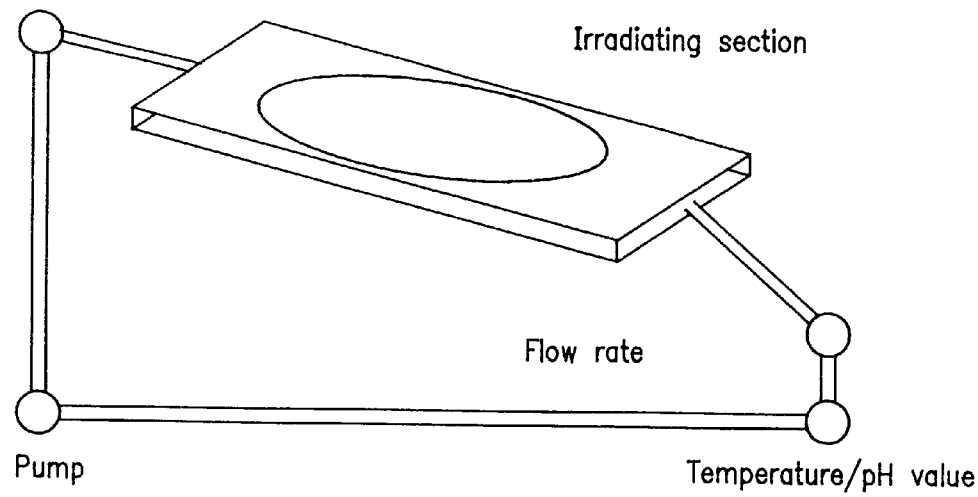
Figure 2:
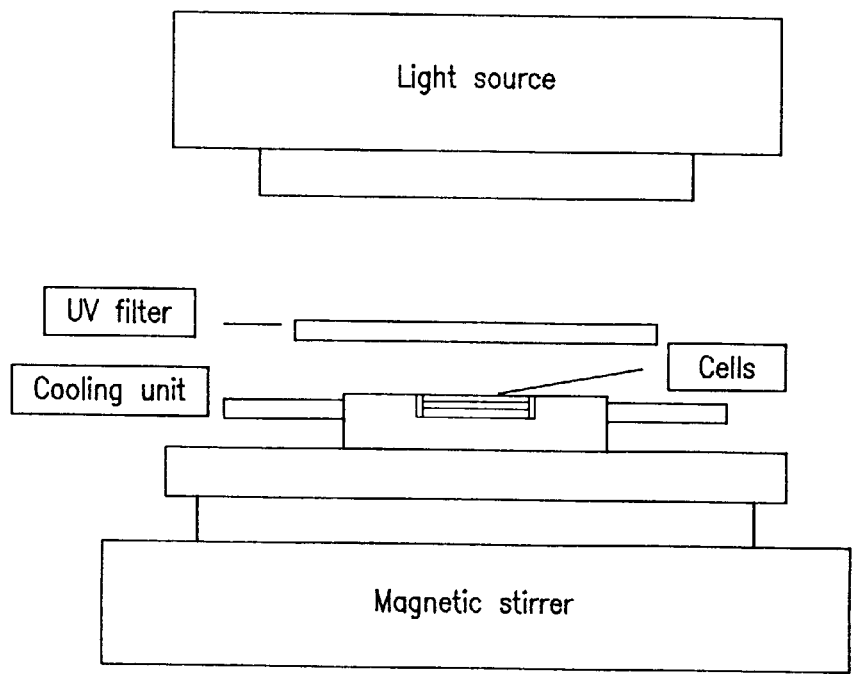
Figure 3:
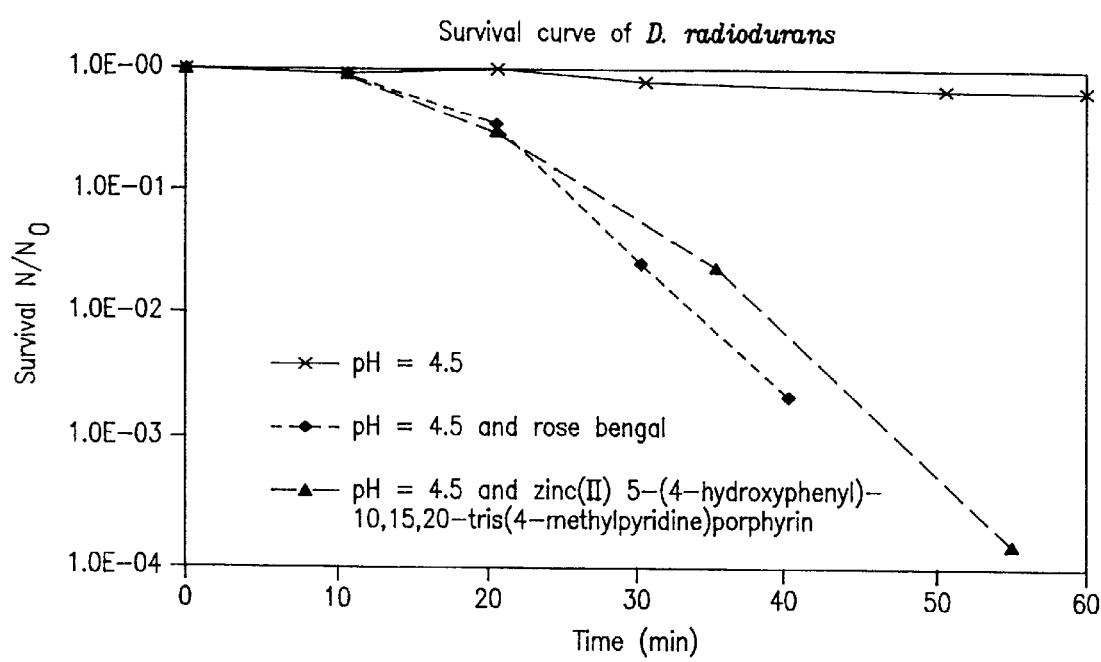

Experiments for the Determination of Singlet Oxygen Production Rates of Different Sensitizers in a Non-Aqueous Medium The same detection system as described in Example 8 was employed except that the solvent water was replaced by anhydrous ethyl acetate. The following results were obtained.

| Dye | Singlet oxygen production rate, $\Delta c(^1O_2)/\Delta t$ [(mol/l)/s] |
|---|---|
| Rose bengal* | $1.7 \cdot 10^{-8}$ |
| Zinc(II) 5-(4-hydroxyphenyl)-10,15,20-tris(4-methylpyridino)-porphyrin, bound to polymethyl methacrylate*** | $4.4 \cdot 10^{-8}$ |

*Comparison, homogeneously dissolved
**obtainable according to Example 6
***obtainable according to Example 4

What is claimed is:

1. Metallated or unmetallated porphyrin derivatives of formula I

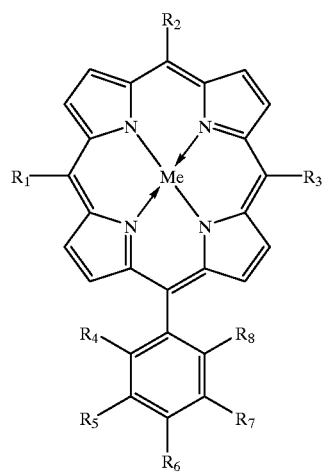

wherein $R_1$, $R_2$ and $R_3$ represent hydrogen, alkyl, aryl, aralkyl or alkaryl, alkyl-, aryl-, aralkyl- or alkarylsulfonate, or pyridine-N-alkyl, -aryl, -alkaryl or -aralkyl each having from 1 to 8 carbon atoms, with the proviso that at least one of $R_1$, $R_2$ or $R_3$ is not hydrogen, alkyl, aryl, aralkyl or alkaryl;

one of $R_4$, $R_5$, $R_6$, $R_7$ and $R_8$ is a hydroxy group, or a polymer residue derived from polyesters, polymethyl methacrylates, polymethacrylic acids, polyacrylic acids and their esters, polymethacrylamides, polyacetals, polyimides, polyamides, copolymers thereof, or their respective monomer units, whereas the others are hydrogen, with the proviso that if one of $R_4$, $R_5$, $R_6$, $R_7$ or $R_8$ is a hydroxy group, at least one of $R_1$, $R_2$ or $R_3$ is hydrogen alkyl, aryl, aralkyl, or alkaryl, alkyl-, aryl-, aralkyl- or alkarylsulfonate; and Me represents a metal cation or saturation with hydrogen atoms.

2. The metallated or unmetallated porphyrin derivative according to claim 1, wherein $R_4$, $R_5$, $R_7$ and $R_8$ each represent hydrogen, and $R_6$ represents a hydroxy group.

3. The metallated or unmetallated porphyrin derivative according to claim 1, wherein pyridine-N-alkyl represents pyridine-N-methyl.

4. The metallated porphyrin according to claim 1, wherein Me represents Zn.

5. A photosensitizer comprising at least one porphyrin derivative of formula I according to claim 1 in an amount of from 0.1 to 10% by weight.

6. The photosensitizer according to claim 5, characterized in that said porphyrin of formula I is present in a polymer matrix in a covalently bonded form.

7. The photosensitizer according to claim 6, characterized in that said polymer matrix comprises fibers, granules, powders, non-woven, woven or knitted fabrics or shaped bodies which may be membranes.

8. A method for initiating photochemical reactions comprising exposing photosensitizers, according to any one of claims 5 to 7, to visible light.

9. The method according to claim 8, wherein said photosensitizers catalyze formation of singlet oxygen from triplet oxygen.

10. Metallated or unmetallated porphyrin derivatives of formula I

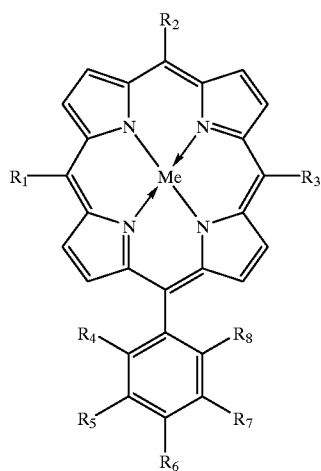

(I)

wherein $R_1$, $R_2$ and $R_3$ represent hydrogen, alkyl, aryl, aralkyl or alkaryl, alkyl-, aryl-, aralkyl- or alkarylsulfonate, or pyridine-N-alkyl, -aryl, -alkaryl or -aralkyl each having from 1 to 8 carbon atoms, with the proviso that at least one of $R_1$, $R_2$ or $R_3$ is not hydrogen, alkyl, aryl, aralkyl or alkaryl;

one of $R_4$, $R_5$, $R_6$, $R_7$ and $R_8$ is a polymer residue derived from polyesters, polymethyl methacrylates, polymethacrylic acids, polyacrylic acids and their esters, polymethacrylamides, polyacetals, polyimides, polyamides, copolymers thereof, or their respective monomer units, whereas the others are hydrogen; and Me represents a metal cation or saturation with hydrogen atoms.

* * * * *